United States Patent
Kobayashi

(10) Patent No.: US 8,039,092 B2
(45) Date of Patent: *Oct. 18, 2011

(54) PATTERN FORMED BODY AND METHOD FOR MANUFACTURING SAME

(75) Inventor: Hironori Kobayashi, Tokyo (JP)

(73) Assignee: Dai Nippon Printing Co., Ltd., Tokyo-to (JP)

( * ) Notice: Subject to any disclaimer, the term of this patent is extended or adjusted under 35 U.S.C. 154(b) by 1057 days.

This patent is subject to a terminal disclaimer.

(21) Appl. No.: 11/472,895

(22) Filed: Jun. 22, 2006

(65) Prior Publication Data

US 2007/0041000 A1    Feb. 22, 2007

(30) Foreign Application Priority Data

Jun. 23, 2005   (JP) .................. 2005-182997

(51) Int. Cl.
  *B41M 5/00*  (2006.01)
(52) U.S. Cl. ............... 428/195.1; 438/8; 438/9; 438/30; 438/57; 438/308; 430/270.1; 430/271.1
(58) Field of Classification Search ............... 428/195.1; 430/8, 9, 30, 57, 308; 438/270.1, 271.1
See application file for complete search history.

(56) References Cited

U.S. PATENT DOCUMENTS

| | | | |
|---|---|---|---|
| 6,450,635 B1 | 9/2002 | Okabe et al. | |
| 6,803,175 B2 * | 10/2004 | Kobayashi | 430/322 |
| 7,172,912 B2 * | 2/2007 | Toyoda | 438/30 |
| 7,335,451 B2 * | 2/2008 | Kobayashi et al. | 430/7 |
| 7,390,597 B2 * | 6/2008 | Kobayashi | 430/7 |
| 7,597,968 B2 * | 10/2009 | Kobayashi | 428/690 |
| 2002/0014470 A1 | 2/2002 | Okada et al. | |
| 2004/0132946 A1 * | 7/2004 | Yamashita et al. | 528/12 |
| 2007/0128738 A1 * | 6/2007 | Kobayashi et al. | 438/8 |

FOREIGN PATENT DOCUMENTS

| | | |
|---|---|---|
| JP | 2000-187111 | 7/2000 |
| JP | 2001-074928 A | 3/2001 |
| JP | 2001-0343518 A | 12/2001 |
| JP | 2003-195029 A | 7/2003 |
| JP | 2004-333914 A | 11/2004 |

* cited by examiner

*Primary Examiner* — Bruce H Hess
*Assistant Examiner* — Tamra L Amakwe
(74) *Attorney, Agent, or Firm* — Ladas & Parry LLP

(57) ABSTRACT

A main object of the present invention is to provide a pattern formed body capable of forming highly precise functional parts on various base materials, and a method for manufacturing the same. To achieve the object, the present invention provides a method for manufacturing a pattern formed body, having a plasma radiating step of radiating plasma to a patterning substrate having: a base material; an intermediate layer formed on the base material and containing a silane coupling agent or a polymer of the silane coupling agent; and a resin layer formed in a pattern form on the intermediate layer, wherein a fluorine gas is used as an introduction gas to radiate the plasma from the resin layer side.

4 Claims, 1 Drawing Sheet

PATTERN FORMED BODY AND METHOD FOR MANUFACTURING SAME

BACKGROUND OF THE INVENTION

1. Field of the Invention

The present invention relates to a pattern formed body which is capable of forming a highly precise functional part and is used to manufacture such as a color filter, a microlens, an organic electroluminescent (hereinafter, may be referred to as an organic EL) element, or a cell culturing substrate; a method for manufacturing the same; and so on.

2. Description of the Related Art

Conventionally, various methods have been suggested as a method for manufacturing a pattern formed body wherein various patterns such as designs, images, characters, and circuits are formed on a base material. For example, the following is used: lithography, offset printing, or a printing process wherein a lithographic original plate using a heat mode recording material is formed. There is also known, for example, a method for manufacturing a pattern formed body by photolithography of radiating light in a pattern form to a photoresist layer applied on a base material and developing the photoresist after the radiation to perform etching, or of using a material having functionality as a photoresist and radiating light to the photoresist so as to form a target pattern directly.

However, the above-mentioned printing processes have a problem such as that at the time of manufacturing a highly precise pattern formed body used in, for example, a color filter, only a low location accuracy is attained. Thus, it is difficult to use the printing processes. The above-mentioned photolithography has a problem that it becomes necessary to treat waste liquid since it is necessary to use a photoresist and further develop the resist with a developing solution or perform etching after radiation of light to the resist, and other problems. When a functional material is used as a photoresist to form a functional part, there is caused a problem that the functional part is deteriorated by such as an alkaline solution that is used in development.

Thus, as a method for forming a colored layer of a color filter or the like, suggested is a method of forming a bank made of a resin on a base material made of, such as an inorganic material, radiating plasma to the entire surface thereof while using a fluorine compound as an introduction gas to make only the bank liquid repellent, and causing a colored layer forming coating solution to stay between individual portions of the bank, thereby forming a colored layer (Japanese Patent Application Laid-Open (JP-A) No. 2000-187111). This is a method using the fact that when plasma treatment is conducted using a fluorine compound as an introduction gas, the fluorine can be introduced into only an organic material but not into any inorganic material. However, in this method, as the base material, one made of an organic material cannot be used and one made of an inorganic material is used; therefore, there is caused a problem that the adhesive property between the bank or the functional part of a colored layer formed by using the bank and the base material becomes low. Additionally, for example, even if a base material made of an organic material is used, there arise a problem by the above-mentioned plasma radiation that the adhesive property between the base material and the bank of the resin layer declines, and other problems.

SUMMARY OF THE INVENTION

Thus, it is desired to provide a pattern formed body capable of forming highly precise functional parts on various base materials, and a method for manufacturing the same.

The invention provides a method for manufacturing a pattern formed body, having a plasma radiating step of radiating plasma to a patterning substrate having: a base material; an intermediate layer formed on the base material and containing a silane coupling agent or a polymer of the silane coupling agent; and a resin layer formed in a pattern form on the intermediate layer, wherein a fluorine gas is used as an introduction gas to radiate the plasma from the resin layer side.

In the present invention, when the above-mentioned plasma radiation is performed, the fluorine gas can be introduced onto the resin layer, so that the upper face of the resin layer can be rendered a region having liquid repellency. At this time, in a region where the intermediate layer is exposed, a Si—C bond of the silane coupling agent or the polymer thereof is broken through the plasma radiation, whereby an organic group bonded to the Si element is removed and an OH group or the like is introduced thereto. Thus, the region is rendered a lyophilic region. Consequently, according to the invention, a difference in wettability between the resin layer and the region where the intermediate layer is exposed can be made large. The use of this difference in the wettability makes it possible to manufacture a pattern formed body capable of forming a functional part highly precisely only in the region where the intermediate layer is exposed. In the invention, the intermediate layer is formed; therefore, not only a base material made of an inorganic material but also a base material made of an organic material can be used as the above-mentioned base material. Additionally, the invention has an advantage that the adhesive property between the base material and the resin layer can be made good even if a base material made of an inorganic material is used as the above-mentioned base material. Additionally, in the plasma radiating step, the adhesive property between the base material and the resin layer is not lowered since the intermediate layer is formed.

The invention also provides a pattern formed body having: a base material; an intermediate layer formed on the base material and containing a silane coupling agent or a polymer of the silane coupling agent; and a liquid repellent resin layer formed in a pattern form on the intermediate layer and containing a fluorine in its surface.

According to the pattern formed body of the invention, a difference in wettability between the upper face of the liquid repellent resin layer and a region where the intermediate layer is exposed is used to make it possible to form a functional part highly precisely only on the region where the intermediate layer is exposed. Moreover, in the invention, the intermediate layer is formed; therefore, the invention has an advantage that the adhesive property between the functional part formed on the pattern formed body of the invention and the base material can be made good even if the above-mentioned base material is made of an inorganic material.

The region of the intermediate layer where the liquid repellent resin layer is not formed is preferably rendered a lyophilic region having a contact angle with water, in its surface, of 60° or less.

This makes it possible that a difference in wettability between the upper face of the liquid repellent resin layer and the region where the intermediate layer is exposed is made large, thereby manufacturing a pattern formed body capable of forming a functional part further highly precisely.

The present invention also provides: a color filter, wherein a colored layer is formed on the lyophilic region of the above-mentioned pattern formed body; an organic EL element, wherein an organic EL layer is formed on the lyophilic region of the above-mentioned pattern formed body; and a microlens, wherein a lens is formed on the lyophilic region of the above-mentioned pattern formed body. According to the invention, in the pattern formed body, the region where the liquid repellent resin layer is formed, that is, the liquid repellent region, and the lyophilic region are formed; therefore, the wettability difference therebetween is used to make it possible to manufacture a functional element wherein various functional parts are highly precisely formed only in the lyophilic region. The invention also has an advantage that in this case the adhesive property between the functional part and the base material can be made good.

The invention also provides a cell culturing substrate, wherein the upper face of the lyophilic region of the above-mentioned pattern formed body is used to culture a cell. According to the invention, in the pattern formed body, the liquid repellent region and the lyophilic region are formed; therefore, the wettability difference therebetween is used to make it possible to manufacture a cell culturing substrate for culturing cells in a highly precise pattern only in the lyophilic region.

In the method for manufacturing the pattern formed body of the invention, the wettability difference between the resin layer and the region where the intermediate layer is exposed can be made large since the above-mentioned plasma radiating step is performed. Accordingly, this wettability difference is used to make it possible to manufacture a pattern formed body capable of forming a functional part highly precisely only in the region where the intermediate layer is exposed. Additionally, the invention produces advantages that: as the base material, various ones can be used; and further the adhesive property between the base material and the functional part can be made good.

DESCRIPTION OF THE PREFERRED EMBODIMENT

The present invention relates to a pattern formed body which is capable of forming a highly precise functional part and is used to manufacture such as a color filter, a microlens, an organic EL element, or a cell culturing substrate; a method for manufacturing the same; and so on. Each of them will be described hereinafter.

A. Method for Manufacturing a Pattern Formed Body

First, the method of the invention for manufacturing a pattern formed body is described. The method for manufacturing the color filter is a method having a plasma radiating step of radiating plasma to a patterning substrate having: a base material; an intermediate layer formed on the base material and containing a silane coupling agent or a polymer of the silane coupling agent; and a resin layer formed in a pattern form on the intermediate layer, wherein a fluorine gas is used as an introduction gas to radiate the plasma from the resin layer side.

Figure 1:
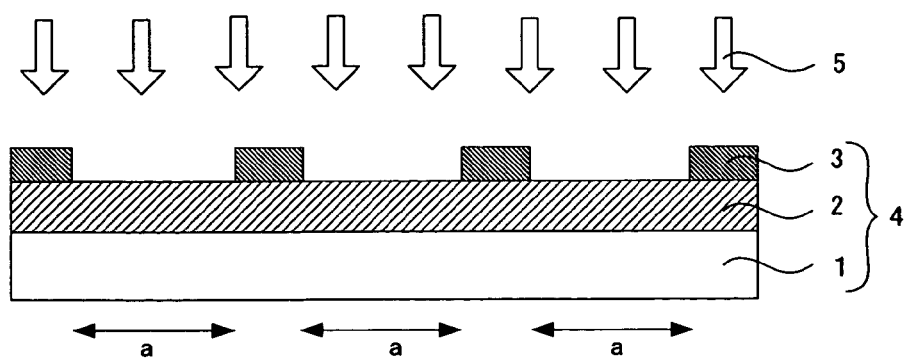
FIG. 1 is a process drawing illustrating an example of a method for manufacturing the pattern formed body of the invention.

As illustrated in, for example, FIG. 1, a method for manufacturing a pattern formed body of the invention is a method of performing a plasma radiating step of radiating plasma 5 to a patterning substrate 4 having: a base material 1; an intermediate layer 2 formed on the base material 1; and a resin layer 3 formed in a pattern form on the intermediate layer 2, wherein a fluorine gas is used as an introduction gas from the side of the resin layer 3 to manufacture a pattern formed body.

According to the invention, the fluorine can be introduced into the surface of the resin layer through the plasma radiating step, so that the resin layer can have liquid repellency. Since the intermediate layer contains the silane coupling agent or the polymer thereof, a region where the intermediate layer is exposed, that is, the region where the resin layer is not formed (for example, the region represented by a in FIG. 1) can be made lyophilic by the plasma radiation in the plasma radiating step. This is because a Si—C bond in the silane coupling agent or the polymer thereof is broken by the plasma radiation, so that an organic group is removed and then OH groups or the like is introduced into the group-removed moiety by water content, oxygen or the like in the atmosphere.

According to the invention, therefore, a difference in wettability between the resin layer and the region where the intermediate layer is exposed is used to make it possible to manufacture a pattern formed body capable of forming the functional part highly precisely only in the region where the intermediate layer is exposed.

As described above, a conventional method of forming a bank on a base material and radiating plasma thereto, using a fluorine compound as an introduction gas has a problem that as this base material, a base material made of an organic material cannot be used for the following reason: when a base material made of an organic material is used as the above-mentioned base material, the fluorine is unfavorably introduced into the upper face of the base material so that it is impossible to permit only the bank to be made liquid repellent. However, according to the invention, even if a base material made of an organic material is used as the above-mentioned base material, only the resin layer can be made liquid repellent since the intermediate layer is formed.

Additionally, in the conventional method, a base material made of an inorganic material is used as the base material; thus, the method has a problem that the adhesive property between the base material and the bank or the functional part formed by using this bank is low. However, according to the invention, the adhesive property between the base material and the resin layer or the functional part formed on the pattern formed body can be made high by the action of such as the silane coupling agent or the polymer thereof contained in the intermediate layer, even if a base material made of an inorganic material is used as the above-mentioned base material. Moreover, the conventional method has a problem that in the case of performing plasma radiation described above, the adhesive property between the base material and the bank may be lowered by the plasma radiation even if a base material made of an organic material is used as the above-mentioned base material. However, according to the invention, since the intermediate layer is formed, the fall in the adhesive property between the base material and the resin layer by the plasma radiating step, can be made small. Thus, the invention has an advantage that by use of various base materials, high-quality pattern formed bodies which can be used for various applications can be manufactured.

The following will describe the plasma radiating step and other steps in the invention.

1. Plasma Radiating Step

The plasma radiating step in the invention is a step of radiating plasma to a patterning substrate having: a base material; an intermediate layer formed on the base material and containing a silane coupling agent or a polymer of the silane coupling agent; and a resin layer formed in a pattern form on the intermediate layer, wherein a fluorine gas is used as an introduction gas to radiate the plasma from the resin layer side.

The method for radiating the plasma in the present step is not particularly limited as long as the method is capable of introducing the fluorine into the resin layer to make the layer liquid repellent, and breaking the Si—C bond in the silane coupling agent or the polymer thereof contained in region with the intermediate layer exposed. For example, the plasma may be radiated under reduced pressure or the atmosphere pressure.

In terms of the plasma radiation, radiation area and the like are not particularly limited as long as the plasma is radiated from the side of the resin layer. For example, the plasma may be radiated to the entire surface of the patterning substrate, or to only a part of the patterning substrate.

Examples of the fluorine compound as the introduction gas used when the plasma is radiated include carbon fluoride ($CF_4$), carbon nitride ($NF_3$), sulfur fluoride ($SF_6$), $C_2Cl_3F_3$, $C_2F_6$, and $C_3F_6$. Conditions for radiating the plasma are appropriately selected in accordance with a device for the radiation and the like.

In the invention, it is particularly preferred to radiate the plasma in the atmosphere pressure since no pressure-reducing device and so on is required, so that advantages are produced from the viewpoint of costs and production efficiency. Conditions for radiating the plasma in the atmosphere are as follows. For example, the power output therefore may be the same as used in an ordinary device for radiating plasma in the atmosphere pressure. The distance between the electrode for the plasma radiated at this time and the above-mentioned patterning substrate is preferably from about 0.2 to 20 mm, more preferably from about 1 to 5 mm. The flow rate of the fluorine compound used as the introduction gas is preferably from about 1 to 100 L/min, more preferably from about 5 to 50 L/min. The transporting rate of the patterning substrate at this time is preferably from about 0.1 to 10 m/min, more preferably from about 0.5 to 5 m/min.

In the present step, the presence of the fluorine introduced in the resin layer can be checked by measuring the ratio of the fluorine element in all elements detected from the surface of the resin layer in analysis with an X-ray photoelectron spectral analyzer (XPS: ESCALAB 220i-XL). The ratio of the fluorine introduced in the resin layer at this time is preferably 10% or more of all the elements detected from the surface of the resin layer.

In the present step, the fluorine is introduced so as to set the contact angle of liquid of the resin layer with water preferably to 61° or more, more preferably to 80° or more, even more preferably to 100° or more for the following reason: if the contact angle with liquid is small, the liquid repellency is insufficient; thus, when the pattern formed body of the invention is used to form a functional element, a functional part forming coating solution for a forming functional part may adhere onto the upper face of the resin layer.

The contact angle of the region where the intermediate layer is exposed with liquid is preferably 60° or less, more preferably 40° or less, even more preferably 20° or less. If the contact angle of the region where the intermediate layer is exposed with water is high, at the time of forming the functional part on the pattern formed body of the invention, the functional part forming coating solution for forming the functional part may be repelled. Thus, it may be difficult to form the functional part highly precisely.

The contact angle with respect to a liquid here is obtained from the results or a graph of the results of measuring (30 seconds after of dropping liquid droplets from a micro syringe) the contact angle with respect to water or liquids having equivalent contact angle to that of water using a contact angle measuring device (CA-Z type manufactured by Kyowa Interface Science, Co., Ltd). Moreover, at the time of the measurement, as the liquids having the various surface tensions, wetting index standard solution manufactured by JUNSEI CHEMICAL CO., LTD. were used.

The following will describe the patterning substrate used in the above-mentioned step.
(Patterning Substrate)

The patterning substrate used in the invention is not particularly limited as long as the patterning substrate is a substrate having a base material, an intermediate layer formed on the base material, and a resin layer formed into a pattern form on the intermediate layer. Each of the constituents used in this patterning substrate will be described hereinafter.
a. Intermediate Layer The intermediate layer used in the invention is first described herein. The intermediate layer is not particularly limited as long as the layer contains a silane coupling agent or a polymer of the silane coupling agent.

In the invention, the layer may consist only of the silane coupling agent or the polymer thereof; or may contain the silane coupling agent or the polymer thereof, and a binder made of an inorganic material.

Specific examples of the silane coupling agent or the polymer thereof which is contained in the intermediate layer include the silane coupling agent or a polymer which is a hydrolysis or cohydrolysis condensation product of at least one compound represented by the following formula:

(Here, Y is alkyl group, fluoroalkyl group, vinyl group, amino group, phenyl group, chloroalkyl group, isocyanate group, epoxy group or an organic group containing them; X is alkoxyl group, acetyl group or halogen; and n is an integer from 0 to 3). Here, the alkoxy group represented by X is preferably methoxy group, ethoxy group, propoxy group, or butoxy group. Moreover, the number of atoms of the entire organic group represented by Y is preferably in a range of 1 to 20, in particular, in a range of 5 to 10.

As the silane coupling agent, specifically, the following can be used: methyltrichlorosilane, methyltribromosilane, methyltrimethoxysilane, methyltriethoxysilane, methyltriisopropoxysilane, methyltri-t-butoxysilane; ethyltrichlorosilane, ethyltribromosilane, ethyltrimethoxysilane, ethyltriethoxysilane, ethyltriisopropoxysilane, ethyltri-t-butoxysilane; n-propyltrichlorosilane, n-propyltribromosilane, n-propyltrimethoxysilane, n-propyltriethoxysilane, n-propyltriisopropoxysilane, n-propyltri-t-butoxysilane; n-hexyltrichlorosilane, n-hexyltribromosilane, n-hexyltrimethoxysilane, n-hexyltriethoxysilane, n-hexyltriisopropoxysilane, n-hexyltri-t-butoxysilane; n-decyltrichlorosilane, n-decyltribromosilane, n-decyltrimethoxysilane, n-decyltriethoxysilane, n-decyltriisopropoxysilane, n-decyltri-t-butoxysilane; n-octadecyltrichlorosilane, n-octadecyltribromosilane, n-octadecyltrimethoxysilane, n-octadecyltriethoxysilane, n-octadecyltriisopropoxysilane, n-octadecyltri-t-butoxysilane; phenyltrichlorosilane, phenyltribromosilane, phenyltrimethoxysilane, phenyltriethoxysilane, phenyltriisopropoxysilane, phenyltri-t-butoxysilane; dimethoxydiethoxysilane; dimethyldichlorosilane, dimethyldibromosilane, dimethyldimethoxysilane, dimethyldiethoxysilane; diphenyldichlorosilane, diphenyldibromosilane, diphenyldimethoxysilane, diphenyldiethoxysilane; phenylmethyldichlorosilane, phenylmethyldibromosilane, phenylmethyldimethoxysilane, phenylmethyldiethoxysilane; trichlorohydrosilane, tribromohydrosilane, trimethoxyhydrosilane, triethoxyhydrosilane, triisopropoxyhydrosilane, tri-t-butoxyhydrosilane; vinyltrichlorosilane, vinyltribromosilane, vinyltrimethoxysilane, vinyltriethoxysilane, vinyltriisopropoxysilane, vinyltri-t-butoxysilane; γ-glycidoxypropylmethyldimethoxysilane, γ-glycidoxypropylmethyldiethoxysilane, γ-glycidoxypropyltrimethoxysilane, γ-glycidoxypropyltriethoxysilane, γ-glycidoxypropyltriisopropoxysilane, γ-glycidoxypropyltri-t-butoxysilane; γ-methacryloxypropylmethyldimethoxysilane, γ-methacryloxypro pylmethyldiethoxysilane,γ-methacryloxypropyltrimethoxysilan e,γ-methacryloxypropyltriethoxysilane,γ-methacryloxypropylt riisopropoxysilane,γ-methacryloxypropyltri-t-butoxysilane;γ-aminopropylmethyldimethoxysilane,γ-aminopropylmethyldietho xysilane,γ-aminopropyltrimethoxysilane,γ-aminopropyltrietho xysilane,γ-aminopropyltriisopropoxysilane,γ-aminopropyltri-t-butoxysilane;γ-mercaptopropylmethyldimethoxysilane, γ-merc aptopropylmethyldiethoxysilane,γ-mercaptopropyltrimethoxysi lane,γ-mercaptopropyltriethoxysilane,γ-mercaptopropyltriiso propoxysilane,γ-mercaptopropyltri-t-butoxysilane;β-(3,4-epo xycyclohexyl) ethyltrimethoxysilane, β-(3,4-epoxycyclohexyl) ethyltriethoxysilane; partially hydrolyzed products thereof; and mixture thereof.

The compound containing a fluoroalkyl group is exemplified below. Any compound that is generally known as a fluorine-based silane coupling agent may be used.
$CF_3 (CF_2)_3 CH_2CH_2Si (OCH_3)_3$;
$CF_3 (CF_2)_5 CH_2CH_2Si (OCH_3)_3$;
$CF_3 (CF_2)_7 CH_2CH_2Si (OCH_3)_3$;
$CF_3 (CF_2)_9 CH_2CH_2Si (OCH_3)_3$;
$(CF_3)_2CF (CF_2)_4 CH_2CH_2Si (OCH_3)_3$;
$(CF_3)_2CF (CF_2)_6 CH_2CH_2Si (OCH_3)_3$;
$(CF_3)_2CF (CF_2)_8 CH_2CH_2Si (OCH_3)_3$;
$CF_3 (C_6H_4) C_2H_4Si (OCH_3)_3$;
$CF_3 (CF_2)_3 (C_6H_4) C_2H_4Si (OCH_3)_3$;
$CF_3 (CF_2)_5 (C_6H_4) C_2H_4Si (OCH_3)_3$;
$CF_3 (CF_2)_7 (C_6H_4) C_2H_4Si (OCH_3)_3$;
$CF_3 (CF_2)_3 CH_2CH_2SiCH_3 (OCH_3)_2$;
$CF_3 (CF_2)_5 CH_2CH_2SiCH_3 (OCH_3)_2$;
$CF_3 (CF_2)_7 CH_2CH_2SiCH_3 (OCH_3)_2$;
$CF_3 (CF_2)_9 CH_2CH_2SiCH_3 (OCH_3)_2$;
$(CF_3)_2CF(CF_2)_4 CH_2CH_2SiCH_3 (OCH_3)_2$;
$(CF_3)_2CF(CF_2)_6 CH_2CH_2Si CH_3(OCH_3)_2$;
$(CF_3)_2CF(CF_2)_8 CH_2CH_2Si CH_3(OCH_3)_2$;
$CF_3 (C_6H_4) C_2H_4SiCH_3 (OCH_3)_2$;
$CF_3 (CF_2)_3 (C_6H_4) C_2H_4SiCH_3 (OCH_3)_2$;
$CF_3 (CF_2)_5 (C_6H_4) C_2H_4SiCH_3 (OCH_3)_2$;
$CF_3 (CF_2)_7 (C_6H_4) C_2H_4SiCH_3 (OCH_3)_2$;
$CF_3 (CF_2)_3 CH_2CH_2Si (OCH_2CH_3)_3$;
$CF_3 (CF_2)_5 CH_2CH_2Si (OCH_2CH_3)_3$;
$CF_3 (CF_2)_7 CH_2CH_2Si (OCH_2CH_3)_3$;
$CF_3 (CF_2)_9 CH_2CH_2Si (OCH_2CH_3)_3$;
$CF_3 (CF_2)_7 SO_2N(C_2H_5) C_2H_4CH_2Si (OCH_3)_3$.

When the intermediate layer consists only of the silane coupling agent or a polymer thereof, the formation of the intermediate layer can be attained by applying this material, which is dispersed in such as a solvent if necessary, onto a base material in a known coating method such as spin coating, spray coating, dip coating, roll coating or bead coating. At this time, the intermediate layer made of the polymer may be formed by hydrolyzing the silane coupling agent with water content in the air to produce a silanol, and then subjecting the silanol to dehydrating polycondensation. The dehydrating polycondensation may be conducted at room temperature. When the polycondensation is conducted at 100° C. or higher, the polymerization degree of the silanol increases, so that the strength of the film surface can be improved.

When the intermediate layer contains a binder, the material used as the binder in the intermediate layer is preferably a material which does not undergo decomposition or the like by plasma radiation. For example, an amorphous silica precursor may be used. This amorphous silica precursor is a silicon compound represented by the general formula $SiX_4$ wherein X is such as halogen, methoxy group, ethoxy group or acetyl group, silanol which is a hydrolyzate thereof, or polysiloxane having an average molecular weight of 3000 or less.

Specific examples thereof include tetraethoxysilane, tetraisopropoxysilane, tetra-n-propoxysilane, tetrabutoxysilane, and tetramethoxysilane. In this case, the intermediate layer can be formed by dispersing, for example, the amorphous silica precursor and the silane coupling agent or the polymer thereof homogeneously into a non-aqueous solvent, applying the dispersion onto a base material, hydrolyzing the applied dispersion with water content in the air in the same manner as described above to produce a silanol, and then subjecting the silanol to dehydrating polycondensation. In terms of the binder, only one kind thereof or a mixture of two or more kinds thereof may be used.

In the invention, the film thickness of the intermediate layer, which is appropriately selected in accordance with the kind of the intermediate layer, is usually 1 μm or less, preferably 0.1 μm or less. The lower limit of the film thickness of the intermediate layer may be the thickness of a monomolecular membrane made of the above-mentioned material(s) since it is sufficient that the layer containing the material(s) is homogeneously formed.

b. Resin Layer

The following will describe the resin layer used in the invention. The resin layer is not particularly limited as long as the layer is formed into a pattern form on the intermediate layer and the fluorine is introduced into through the present step.

The resin layer is appropriately selected in accordance with the usage of the pattern formed body, and may be, for example, a layer having transparency, a layer having light shielding property, or a colored layer. The pattern and the shape of the resin layer are also appropriately selected; in the invention, the width of the resin layer is preferably 1 μm or more, more preferably 5 μm or more. This makes it possible that even if functional parts are formed in adjacent regions with the resin layer sandwiched therebetween, these functional parts are prevented from being linked to each other.

The film thickness of the resin layer is not particularly limited, as long as the film thickness makes it possible that the fluorine is introduced into the resin layer in the present step, whereby the layer expresses liquid repellency. The film thickness, which is appropriately selected in accordance with the usage of the pattern formed body or the like, is set into the range usually from about 0.01 μm to 1 mm, preferably from about 0.1 μm to 0.1 mm.

The material used to form the resin layer is not particularly limited as long as the material is capable of forming the above-mentioned resin layer. For example, the following can be used: a single or mixture made of one or more selected from resins such as polyimide resin, acrylic resin, epoxy resin, polyacrylamide, polyvinyl alcohol, gelatin, casein and cellulose; photosensitive resins; and O/W emulsion type resin compositions such as a product obtained by emulsifying a reactive silicone.

The method for forming the resin layer may be equal to an ordinary method for forming a layer made of the above-mentioned material(s) into a pattern form, and is, for example, printing or photolithography. Alternatively, the method may be a method of arranging, for example, a photocatalyst containing layer, which contains at least a photocatalyst, oppositely to the intermediate layer, radiating energy thereto in the form of a pattern for forming the resin layer, thereby changing the contact angle of the intermediate layer with liquid into a pattern form, and then using this wettability difference to form the resin layer. Such a patterning method using the photocatalyst containing layer may be the same as described in, for example, JP-A No. 2003-195029.

c. Base Material

The following will describe the base material used in the invention. The base material is not particularly limited as long as the base material is a material on which the intermediate layer can be formed, and is appropriately selected in accordance with the usage of the pattern formed body and the like. In the invention, the base material may be made of an organic material or an inorganic material. Specific examples thereof include non-flexible rigid materials such as a quartz glass plate, a Pyrex (registered trademark) plate and a synthetic quartz plate; and flexible materials, which have flexibility, such as a resin film and an optical resin plate.

2. Other Steps

Besides the plasma radiating step, the invention may have, for example, a patterning substrate forming step for forming a patterning substrate.

The pattern formed body manufactured by the invention can be used in: a method for manufacturing a color filter wherein a colored layer is formed in region where the intermediate layer made lyophilic in the plasma radiating step is exposed, a method for forming an organic EL element wherein an organic EL layer is formed in the region made lyophilic, a microlens forming method wherein a lens is formed in the region made lyophilic; a cell culturing substrate wherein the region made lyophilic is used as a cell culturing region; or others.

B. Pattern Formed Body

The following will describe the pattern formed body of the invention. The pattern formed body comprises a base material, an intermediate layer formed on the base material and containing a silane coupling agent or a polymer of the silane coupling agent, and a liquid repellent resin layer formed in a pattern form on the intermediate layer and containing a fluorine in its surface.

Figure 2:
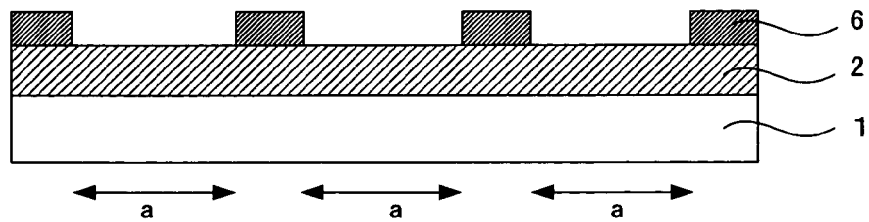
FIG. 2 is a schematic sectional view illustrating an example of the pattern formed body of the invention.

As illustrated in, for example, FIG. 2, the pattern formed body of the invention comprises a base material 1, an intermediate layer 2 formed on the base material 1, and a liquid repellent resin layer 6 formed in a pattern form on the intermediate layer 2 and a fluorine is contained in a surface of the liquid repellent layer 6. The surface of a region where the intermediate layer 2 is exposed (the region represented by a in FIG. 2) is rendered a lyophilic region, and the contact angle thereof with water is preferably set into a predetermined value or less. The lyophilic region referred to in the invention is defined as a region the contact angel of which with liquid is lower than that of a adjacent region by 1° or more.

According to the invention, the liquid repellency of the resin layer can be made high since the surface of the resin layer contains the fluorine. This makes it possible that a difference in wettability between the region where the intermediate layer is exposed and the liquid repellent resin layer is used to manufacture a pattern formed body capable of forming a functional part highly precisely on the lyophilic region.

In the invention, a silane coupling agent or a polymer thereof is contained in the intermediate layer; therefore, the invention has the following advantage: even if a product made of an inorganic material is used as the base material, the adhesive property between the base material and the liquid repellent resin layer or the functional part formed on the pattern formed body of the invention can be made good.

Hereinafter, each of the constituents of the pattern formed body of the invention will be described.

1. Liquid Repellent Resin Layer

The liquid repellent resin layer used in the invention is first described. The liquid repellent resin layer is formed in a pattern form on the intermediate layer which will be detailed later. The layer is not particularly limited as long as the layer contains, in its surface, the fluorine.

The wording "the liquid repellent resin layer contains, in its surface, the fluorine" is defined as a matter that the fluorine is contained in a region which extends from the outermost surface of the liquid repellent resin layer inwards by 5 nm or less. Whether or not the fluorine satisfying this matter is present can be checked by analysis with the above-mentioned X-ray photoelectron spectrometer. At this time, the content by percentage of the fluorine is preferably 10% or more of all elements present in the surface of the liquid repellent resin layer.

The contact angle of the liquid repellent resin layer surface with liquid is preferably 61° or more, more preferably 80° or more, even more preferably 100° or more. This makes the following possible: when the pattern formed body of the invention is used to form a functional element, a functional part forming coating solution for forming a functional part, does not adhere onto the liquid repellent resin layer, so that the functional part is highly precisely formed only in the region where the resin layer is not formed.

The pattern of the liquid repellent resin layer is appropriately selected in accordance with the usage of the pattern formed body, or the like. The film thickness of the liquid repellent resin layer, the width thereof and the like can be made the same as described in the sub-item of the resin layer of the patterning substrate in the above-mentioned item "A. Method for manufacturing pattern formed body".

The method for forming the liquid repellent resin layer may be, for example, a method of forming the layer by such as printing or photolithography, using a liquid repellent forming material having liquid repellency. Particularly preferable is a method of forming a resin layer having no liquid repellency in a pattern form, and then radiating the plasma to the resin layer, using a fluorine compound as an introduction gas. According to this method, at the same time as the fluorine is introduced into the surface of the resin layer, an OH group can be introduced into the surface of the intermediate layer which will be detailed later to make the surface lyophilic. Thus, a pattern formed body can be effectively manufactured. In this case, the fluorine is introduced only into the surface of the liquid repellent resin layer. The method for forming this liquid repellent resin layer may be the same method as described about the plasma radiating step in the above-mentioned item "A. Method for manufacturing pattern formed body". Thus, detailed description thereof will not be described herein.

2. Intermediate Layer

Next, the intermediate layer used in the invention is described. The intermediate layer is a layer formed on the base material that will be detailed later and further contains a silane coupling agent or a polymer thereof. A region where the resin layer is not formed is rendered a region made lyophilic. The contact angle of the upper face thereof with water is preferably set to a predetermined value or less.

The contact angle of the lyophilic region with liquid, specifically, with water is preferably 60° or less, more preferably 40° or less, even more preferably 20° or less. When the contact angle of the region with liquid is high, at the time of forming the functional part onto the lyophilic region of the pattern formed body of the invention, the region may repel a functional part forming coating solution for forming the functional part. Thus, the functional part forming coating solution does not wet or spread sufficiently. As a result, it may become difficult to form the functional part.

The intermediate layer used in the invention may consist only of a silane coupling agent or a polymer thereof, or further comprise a binder, and the like. The silane coupling agent, the polymer thereof, or the binder contained in such an intermediate layer may be the same as described in the sub-item of the intermediate layer of the item "A. Method for manufacturing pattern formed body". The method for forming the lyophilic region may be a method of radiating the plasma to the region where the intermediate layer is exposed, as described in the above-mentioned item "A. Method for manufacturing pattern formed body".

3. Base Material

The base material used in the invention is not particularly limited as long as the base material is a material on which the intermediate layer can be formed, and is appropriately selected in accordance with the usage of the pattern formed body, and the like. This base material may consist, for example, of an organic material or an inorganic material. Specifically, there can be used a non-flexible rigid material such as a quartz glass plate, a Pyrex (registered trademark) plate or a synthetic quartz plate; or a flexible material, which has flexibility, such as a resin film or an optical resin plate.

4. Pattern Formed Body

The pattern formed body of the invention is not particularly limited as long as the body has the base material, the intermediate layer and the resin layer, and may further have, for example, a light shielding layer if necessary.

The pattern formed body of the invention can be used in: a method for manufacturing a color filter wherein a colored layer is formed in the lyophilic region, a method for manufacturing an organic EL element wherein an organic EL layer is formed in the lyophilic region, a method for forming a microlens wherein a lens is formed in the lyophilic region; a cell culturing substrate wherein the lyophilic region is used as a cell culturing region, which will be detailed below.

C. Color Filter

Next, the color filter of the invention is described. The color filter of the invention is a product wherein a colored layer is formed on the lyophilic region of the above-mentioned pattern formed body. On the above-mentioned pattern formed body are formed the lyophilic region where the intermediate layer is exposed and the liquid repellent resin layer with a high liquid repellency; therefore, a wettability difference therebetween is used to make it possible to form a colored layer only in the lyophilic region with a high precision. Since the intermediate layer is formed, given is an advantage that even if the base material is made of an inorganic material, the adhesive property between the colored layer and the base material can be made high.

In the invention, the liquid repellent resin layer can be used as a black matrix layer by using a material having a light shielding property for the formation of this liquid repellent resin layer; it is therefore unnecessary to form a different black matrix layer separately, so that the color filter can be effectively produced. In terms of each of the members of the color filter of the invention, the material thereof, the manufacturing method thereof, and the like may be the same as those in ordinary color filters. Thus, description thereof will not be described herein.

D. Organic EL Element

Next, the organic EL element of the invention is described. The organic EL element of the invention is a product wherein an organic EL layer is formed on the above-mentioned lyophilic region. On the above-mentioned pattern formed body are formed the lyophilic region where the intermediate layer is exposed and the liquid repellent resin layer with a high liquid repellency; therefore, a wettability difference therebetween is used to make it possible to form an organic EL layer only in the lyophilic region with a high precision. Since the intermediate layer is formed, given is an advantage that even if the base material is made of an inorganic material, the adhesive property between the organic EL layer and the base material can be made high.

The organic EL layer is a layer made of one or more organic layers which comprise at least one light emitting layer. In other words, the organic EL layer is a layer which comprises at least one light emitting layer, and has a layer structure having one or more organic layers. When the organic EL layer is formed through a wet process based on coating, it is usually difficult to laminate many layers because of the use of solvents; thus, in many cases, the organic layer is made of one or two organic layers. However, the organic layer can be made to have a larger number of layers by devising organic materials therefor, or combining the coating with vacuum evaporation.

In terms of each of the members of the organic EL element of the invention, the material thereof, the manufacturing method thereof, and the like may be the same as those in ordinary organic EL elements. Thus, description thereof will not be described herein.

E. Microlens

Next, the microlens of the invention is described. The microlens of the invention is a product wherein a lens is formed on the above-mentioned lyophilic region. On the above-mentioned pattern formed body are formed the lyophilic region where the intermediate layer is exposed and the liquid repellent resin layer with a high liquid repellency; therefore, a wettability difference therebetween is used to make it possible to form a lens only in the lyophilic region with a high precision. Since the intermediate layer is formed, given is an advantage that even if the base material is made of an inorganic material, the adhesive property between the lens and the base material can be made high.

In terms of each of the members of the microlens of the invention, the material thereof, the manufacturing method thereof, and the like may be the same as those in ordinary microlens. Thus, description thereof will not be described herein.

F. Cell Culturing Substrate

Next, the cell culturing substrate of the invention is described. The cell culturing substrate is a product wherein the lyophilic region is used to culture a cell. According to the invention, no cell adheres onto the liquid repellent resin layer by the liquid repellency of the upper face of the liquid repellent resin layer. This makes it possible to culture cells only on the lyophilic region, so that the cells can be cultured into the form of a highly precise pattern.

In terms of other members used in the cell culturing substrate of the invention, the cells to be cultured, and the like may be the same as those in ordinary cell culturing substrates. Thus, description thereof will not be described herein.

The invention is not limited to the above-mentioned embodiments. The embodiments are merely illustrative, and any embodiment that has substantially the same structure as embodies the technical conception recited in the claims for the present invention and that produces the same effects and advantages as the above-mentioned embodiments produce is included in the technical scope of the invention.

EXAMPLES

<1. Formation of an Intermediate Layer>

Mixed and stirred for 5 hours were 1.5 g of decyltrimethoxysilane, 5 g of tetramethoxysilane, and 2 g of 0.1 N hydrochloric acid. The resultant was diluted 10 times with isopropanol, and then the solution was uniformly coated onto a 370 mm×470 mm×0.7 mm glass substrate with a spin coater, so as to yield an intermediate layer having a film thickness of 0.1 µm.

<2. Formation of a Resin Layer>

A black resist containing carbon black (V-259 BK resist, manufactured by Nippon Steel Chemical Co., Ltd.) was coated onto the glass substrate, and the resultant was exposed to light, developed and subjected to post-baking treatment to form a resin layer with a light shielding property having a film thickness of 1.0 µm, a width of 20 µm, and an opening part of 280 µm squares.

<3. Atmospheric Fluorine Plasma Step>

$CF_4$ and $N_2$ were caused to flow onto the substrate at 10 L/min, and 20 L/min, respectively. This treatment was conducted twice at a transporting rate of 0.5 m/min, so as to manufacture a pattern formed body. At this time, the power output was set to 190 V/4.8 A. The contact angles of the upper face of the resin layer and that of the intermediate layer (the opening part) with water were measured. As a result, the contact angle of the resin layer was 105°, and that of the opening part was 7°.

<4. Formation of a Colored Layer>

A piezoelectrically driving ink jet device was used to jet a red thermosetting ink (viscosity: 5 cP) to the opening part, which were made hydrophilic, so as to have a varied wettability, in the pattern formed body. The resultant was then subjected to heating treatment to yield a red colored layer (thickness: 1.5 µm) on the substrate. The colored layer wetted and spread onto wall faces of the resin layer, and white spots were not generated. The above-mentioned viscosity was a value measured with a viscometer, VIBROVISCOMETER CJV 5000 (manufactured by A & D Co., LTD.) at a temperature of 20° C. Next, blue and green colored layers were formed in the same way. As a result, a color filter was formed wherein no white spots were generated in the blue and the green color layers in the same manner as in the red colored layer.

What is claimed is:

1. A pattern formed body comprising:
   a base material;
   an intermediate layer formed on the base material and containing a silane coupling agent or a polymer of the silane coupling agent; and
   a liquid repellent resin layer formed in a pattern form on the intermediate layer, wherein the liquid repellent resin layer consists of a single member or a mixture of members selected from the group consisting of resins such as polyimide resin, acrylic resin, epoxy resin, polyacrylamide, polyvinyl alcohol, gelatin, casein and cellulose; and
   the liquid repellent resin layer contains, in its surface, a fluorine and expresses liquid repellency.

2. The pattern formed body according to claim 1, wherein a region of the intermediate layer where the liquid repellent resin layer is not formed is a lyophilic region having a contact angle with water of 60° or less.

3. A color filter, wherein a colored layer is formed on a lyophilic region of the pattern formed body according to claim 1.

4. A color filter, wherein a colored layer is formed on the lyophilic region of the pattern formed body according to claim 2.

* * * * *